(12) United States Patent
Mâitre et al.

(10) Patent No.: US 8,152,743 B2
(45) Date of Patent: Apr. 10, 2012

(54) ACCESSORY FOR APEX LOCATING APPARATUS

(75) Inventors: Luc Mâitre, Epauvillers (CH); Robert Bachmann, Colombier (CH)

(73) Assignee: Bien-Air Holding SA, Bienne (CH)

(*) Notice: Subject to any disclaimer, the term of this patent is extended or adjusted under 35 U.S.C. 154(b) by 523 days.

(21) Appl. No.: 12/096,319

(22) PCT Filed: Dec. 5, 2005

(86) PCT No.: PCT/EP2005/013027
§ 371 (c)(1),
(2), (4) Date: Jun. 5, 2008

(87) PCT Pub. No.: WO2007/065454
PCT Pub. Date: Jun. 14, 2007

(65) Prior Publication Data
US 2008/0261167 A1 Oct. 23, 2008

(51) Int. Cl.
*A61B 5/00* (2006.01)
*A61B 5/103* (2006.01)
*A61B 5/117* (2006.01)
*A61C 1/00* (2006.01)
*A61C 19/04* (2006.01)

(52) U.S. Cl. .......... 600/590; 600/300; 600/587; 433/27; 433/72

(58) Field of Classification Search ............... 600/300, 600/587, 590; 433/27, 72
See application file for complete search history.

(56) References Cited

U.S. PATENT DOCUMENTS

| | | | |
|---|---|---|---|
| 6,866,509 B2 * | 3/2005 | Jensen | 433/215 |
| 7,014,461 B2 * | 3/2006 | Weinstein | 433/76 |
| 7,354,402 B2 * | 4/2008 | Hoarau et al. | 600/443 |
| 2003/0044755 A1 * | 3/2003 | Jensen | 433/215 |
| 2004/0146830 A1 * | 7/2004 | Weinstein | 433/76 |
| 2005/0221252 A1 * | 10/2005 | Hoarau et al. | 433/31 |
| 2006/0154199 A1 * | 7/2006 | Maxwell et al. | 433/72 |
| 2008/0090199 A1 * | 4/2008 | Noguchi et al. | 433/29 |

FOREIGN PATENT DOCUMENTS

| | | |
|---|---|---|
| EP | 1 563 803 A1 | 8/2005 |
| JP | 11-99129 | 4/1999 |
| WO | 2005/070325 A1 | 8/2005 |

OTHER PUBLICATIONS

International Search Report issued in corresponding application No. PCT/EP2005/013027, completed Jun. 27, 2006 and mailed Jul. 5, 2006.

* cited by examiner

*Primary Examiner* — Max Hindenburg
*Assistant Examiner* — Sean Dougherty
(74) *Attorney, Agent, or Firm* — Griffin & Szipl, P.C.

(57) ABSTRACT

The invention relates to an accessory for an apex locating apparatus, characterized in that it comprises a fitting (16) held with the aid of electrically conducting fastening means (20, 50) to the tooth to be treated or to a neighbouring tooth (14) and which comprises first means (36, 54) for wire-based electrical connection (44) between the apex locating apparatus (2) and the endodonty tool (46), and second means (28, 52) for wire-based electrical connection (34) between said apparatus (2) and the patient. The invention also relates to such an accessory characterized in that it comprises means for wireless electrical connection between said fitting and said apex locating apparatus.

24 Claims, 5 Drawing Sheets

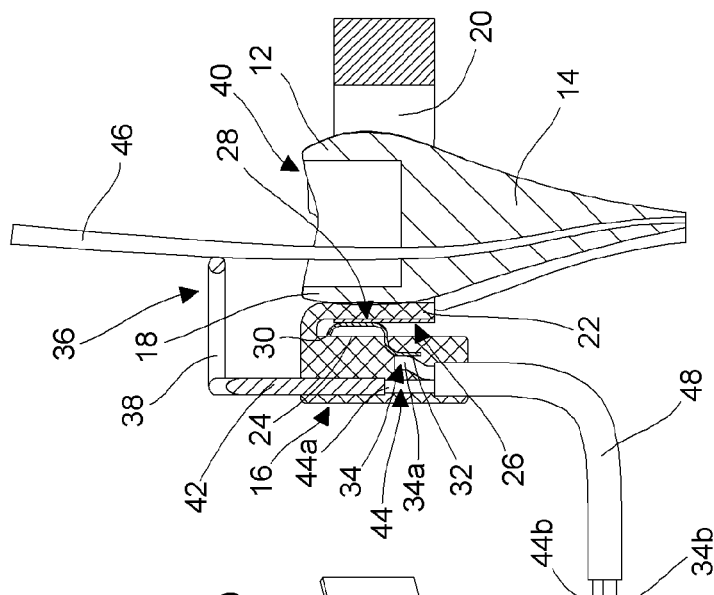
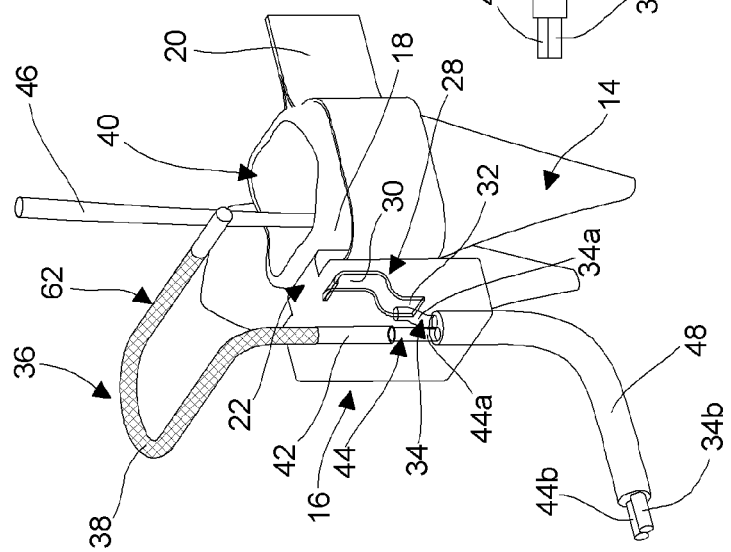
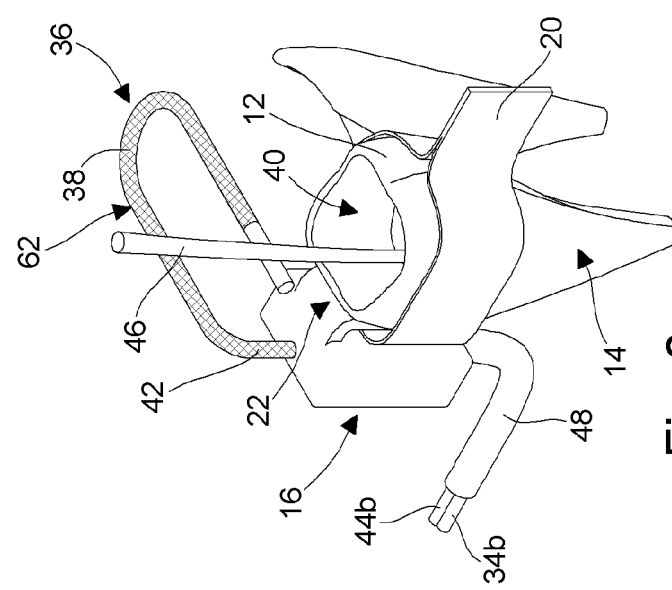

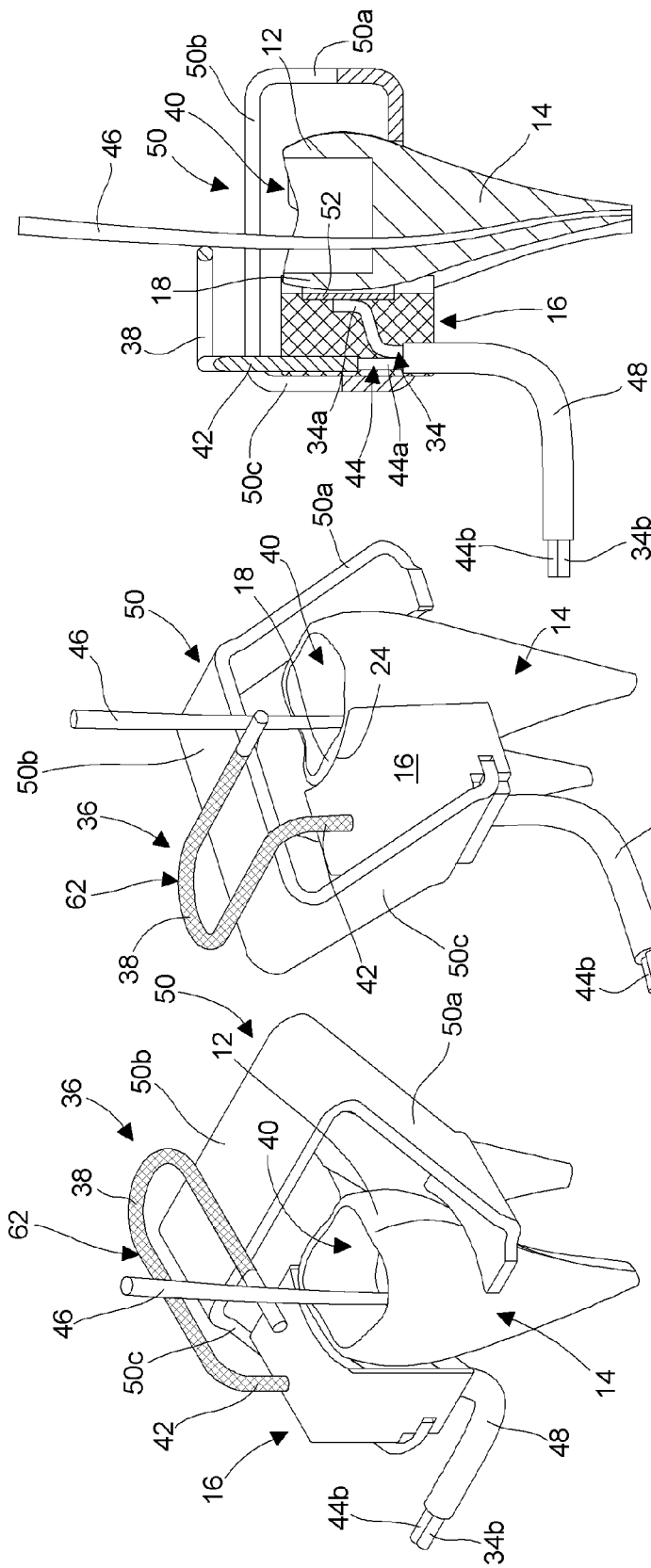

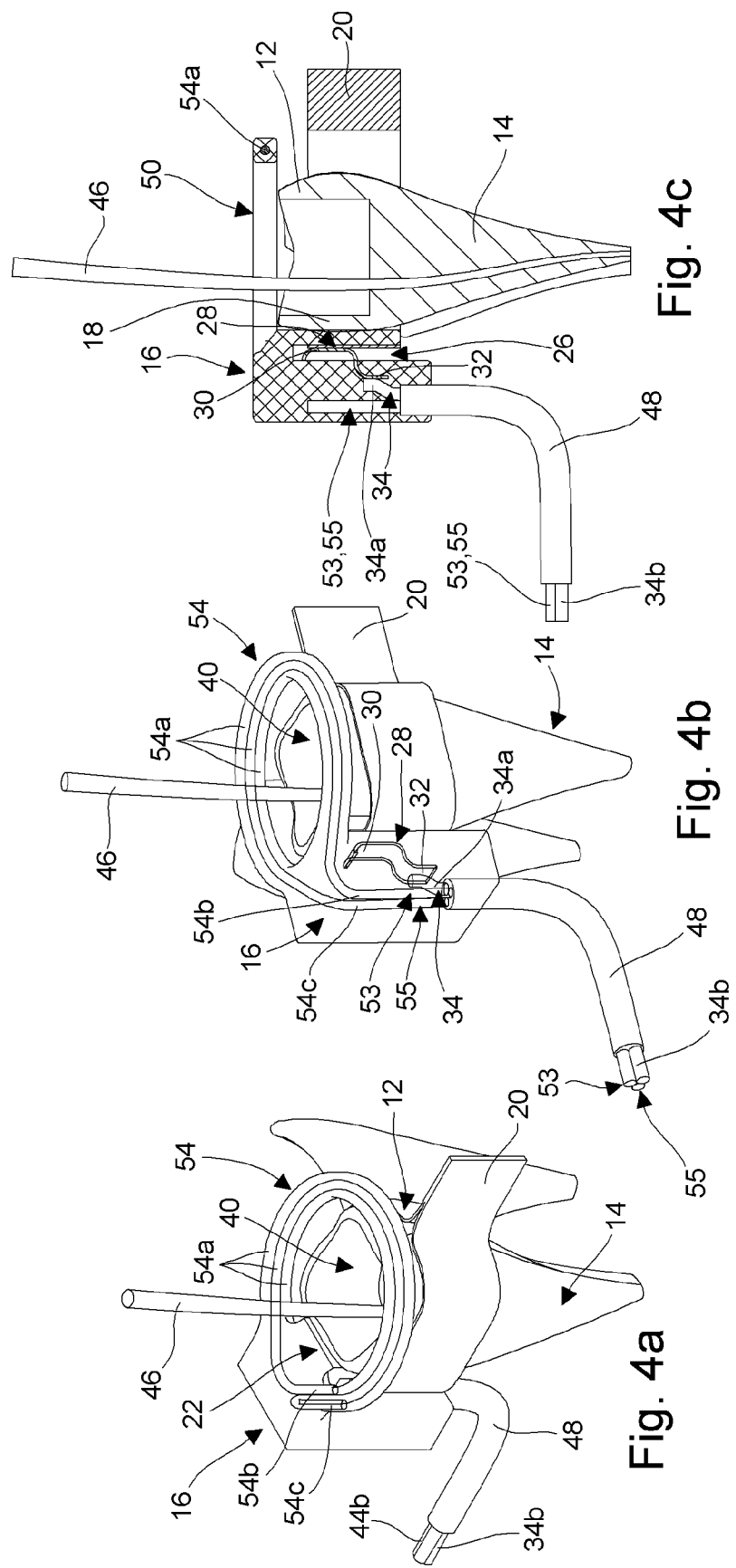

ACCESSORY FOR APEX LOCATING APPARATUS

This is a National Phase Application in the United States of International Patent Application No. PCT/EP2005/013027 filed Dec. 5, 2005, the entire disclosures of which is hereby incorporated by reference.

FIELD OF THE INVENTION

The present invention concerns an accessory for an apex locator device.

BACKGROUND OF THE INVENTION

The main problem encountered in endodontics during root canal treatment is being able to reach as accurately as possible the apical foramen of the root without perforating it. It is thus necessary to be able to measure the length of the root canals. Several methods exist for this purpose.

The best known and most widespread method is the tactile approach. The practitioner evaluates the length of the root canal as he gradually inserts his file into the canal. This manual technique does not require any special tools but relies entirely upon the dexterity of the practitioner.

Another method consists in taking X-rays of the tooth requiring treatment. By analysing the X-ray, the practitioner can judge the geometry of the root canals and identify the position of the apical foramen. It is, however, not unusual for the position of the apex revealed by the X-ray not to coincide with the position of the anatomical apical foramen, hence the risk of X-ray interpretation errors.

Finally, there is a third method which relies upon electronic apex locators. Used in endodontics since the end of the nineteen sixties, these apparatus rely on the principle according to which the electrical features of a human root canal are identical from one person to another. These electronic apex locator devices can be classed in three categories according to the nature of the electrical parameter that is measured.

A first category of these apparatus operates in accordance with the principle of resistance measurement. In fact, in 1962, it was demonstrated that the electrical resistance of a human root canal might reach 6.5Ω. Thus, a constant electrical resistance of 6.5Ω is obtained between a first electrode connected to an endodontic file at the moment that the latter reaches the anatomical apex and a second electrode connected to an oral mucosa.

A second category of apex locator apparatus operates in accordance with the principle of impedance measurement. In fact, it was observed that the root canal developed impedance caused by the presence of hyper-mineralised dentine along the canal, with this impedance increasing all the way along the root canal to reach a maximum at the apical constriction. As soon as the ligament is touched, the impedance drops, which can be electronically detected.

A third category of apex locator apparatus operates in accordance with the principle of frequency measurement. These apparatus measure the impedance of the dentine of the root canal by using two different frequencies and calculate the resulting impedance ratio. At the coronary part of the tooth, the impedance resulting from the two applied frequencies do not vary much, such that their ratio tends towards 1. At the apical part of the tooth, the difference in impedance between the two frequencies increases to reach its maximum value at the cemento-dentinal junction. The ratio tends towards zero at that place.

Whether the apex locator apparatus relies on measuring a resistance, impedance or frequency, an electrical connection has to be established between the apparatus and the practitioner's tool on the one hand, and between the patient and said apparatus on the other hand. This wiring is shown schematically in FIG. 1 annexed to this patent application, which shows an apex locator system based on the resistance measurement principle. Designated as a whole by the reference numeral 1, this system includes an apex locator apparatus 2, which can operate in accordance with any of the three methods for detecting the tooth apex position (resistance, impedance or frequency) and which is connected to an endodontic file 4 via an electrode 6 and to a contact terminal 8 via an electrode 10. The contact terminal 8 is hook shaped so as to be able to be hooked, for example, to the patient's lip 9. It goes without saying that endodontic file 4 could be replaced by a contra-angle if the practitioner is performing a mechanised and not a manual operation. There are thus two wires that pass from the resistance measuring apparatus: one that connects the apparatus to the file or contra-angle and the other that connects the apparatus to the patient. The presence of these two wires can be inconvenient for the practitioner whose movements are limited and who is liable to become caught in one of the wires. In order to overcome this problem, it has already been proposed to fit the contra-angle with means securing the wire that connects the latter to the apex locator apparatus. However, in that case, the practitioner is obliged to purchase a contra-angle solely for endodontic use, which is expensive.

It is an object of the present invention to overcome the aforementioned drawbacks, in addition to others, by providing an apex locator apparatus accessory that limits the inconvenience caused by the electrical connecting wires.

SUMMARY OF THE INVENTION

The present invention therefore concerns an accessory for an apex locator apparatus, characterized in that it includes a fitting held on the tooth to be treated or on a neighbouring tooth by securing means, which includes means for the electrical connection between the apex locator apparatus and the endodontic tool.

According to a first embodiment of the invention, the electrical connecting means are wireless connecting means.

Owing to these features, the present invention provides an accessory for an apex locator apparatus which totally omits any wired connection between the endodontic tool and the apex locator apparatus on the one hand, and between said apex locator apparatus and the patient on the other hand, such that the practitioner is completely free to move, with no risk of becoming caught on a wire. Moreover, the fitting is of a universal type, able to be utilised with any type of apex locator apparatus, independently of the detection principle employed. The fitting according to the invention also does not require the use of a specific endodontic tool, which allows the practitioner to make substantial economies. Finally, the fitting according to the invention will preferably be for a single use, which avoids problems linked to sterilisation of the dental tool after use.

According to a second embodiment of the invention, the fitting includes first means for the wired electrical connection between the apex locator apparatus and the endodontic tool, and second means for the wired electrical connection between said apparatus and the patient.

Owing to these features, the present invention provides a fitting that groups the electrical connection means between the apex locator apparatus and the endodontic tool on the one hand and between the apparatus and the patient on the other hand. The two connecting wires that run between the apex locator apparatus and the fitting can thus be united in a single sheath, which frees the practitioner's movements, in particular preventing the practitioner from becoming caught in a wire.

The fitting can be held by means of a tightening band. This may be a part especially designed for holding the fitting according to the invention. However, it is preferable to use a tightening band which every practitioner has available and which is commonly used for placing dental amalgams, which avoids multiplying the number of parts necessary for implementing the invention.

The fitting may also be held by means of an elastically deformable part. The advantage of such a part lies in the fact that it is self tightening, in other words it spontaneously holds the fitting between against the tooth by elastic deformation, without requiring any screwing or tightening. This part thus makes it simpler and quicker to secure the fitting.

According to a complementary feature of the invention, the fitting includes a second contact strip for establishing the electrical contact between the patient and the apex locator apparatus, and means for establishing an electrical connection between the endodontic tool and said apex locator apparatus, the second contact strip and the connecting means being connected to an electrical connector belonging to the fitting, on which the wired connections between said apex locator apparatus and said fitting are connected.

According to a first variant, the electrical connecting means between the endodontic tool and the apex locator apparatus take the form of a flange which ensures the contact via elastic deformation.

According to a second variant, the electrical connecting means between the endodontic tool and the apex locator apparatus take the form of an induction coil which surrounds the tool so as to ensure a contactless connection.

BRIEF DESCRIPTION OF THE DRAWINGS

Other features and advantages of the present invention will appear more clearly from the following detailed description of an example embodiment of the fitting according to the invention, this example being given purely by way of non-limiting illustration, with reference to the annexed drawing, in which:

FIG. 2A is a perspective view of the posterior face of a tooth fitted with a fitting according to the invention held against the tooth by means of a tightening band;

FIG. 2B is a perspective view of the anterior face of the tooth shown in FIG. 2A;

FIG. 2C is a transverse cross-section of the tooth and the fitting thereof shown in FIGS. 2A and 2B;

FIGS. 3A, 3B and 3C are similar views to those of FIGS. 2A, 2B and 2C respectively, the fitting being held against the tooth by means of a flange capable of being elastically deformed;

FIGS. 4A, 4B and 4C are similar views to those of FIGS. 2A, 2B and 2C respectively in which the electrical connecting means between the endodontic tool and the apex locator apparatus take the form of an induction coil which surrounds the tool so as to ensure a contactless connection.

DETAILED DESCRIPTION OF THE ILLUSTRATIVE EMBODIMENTS

Figure 1:
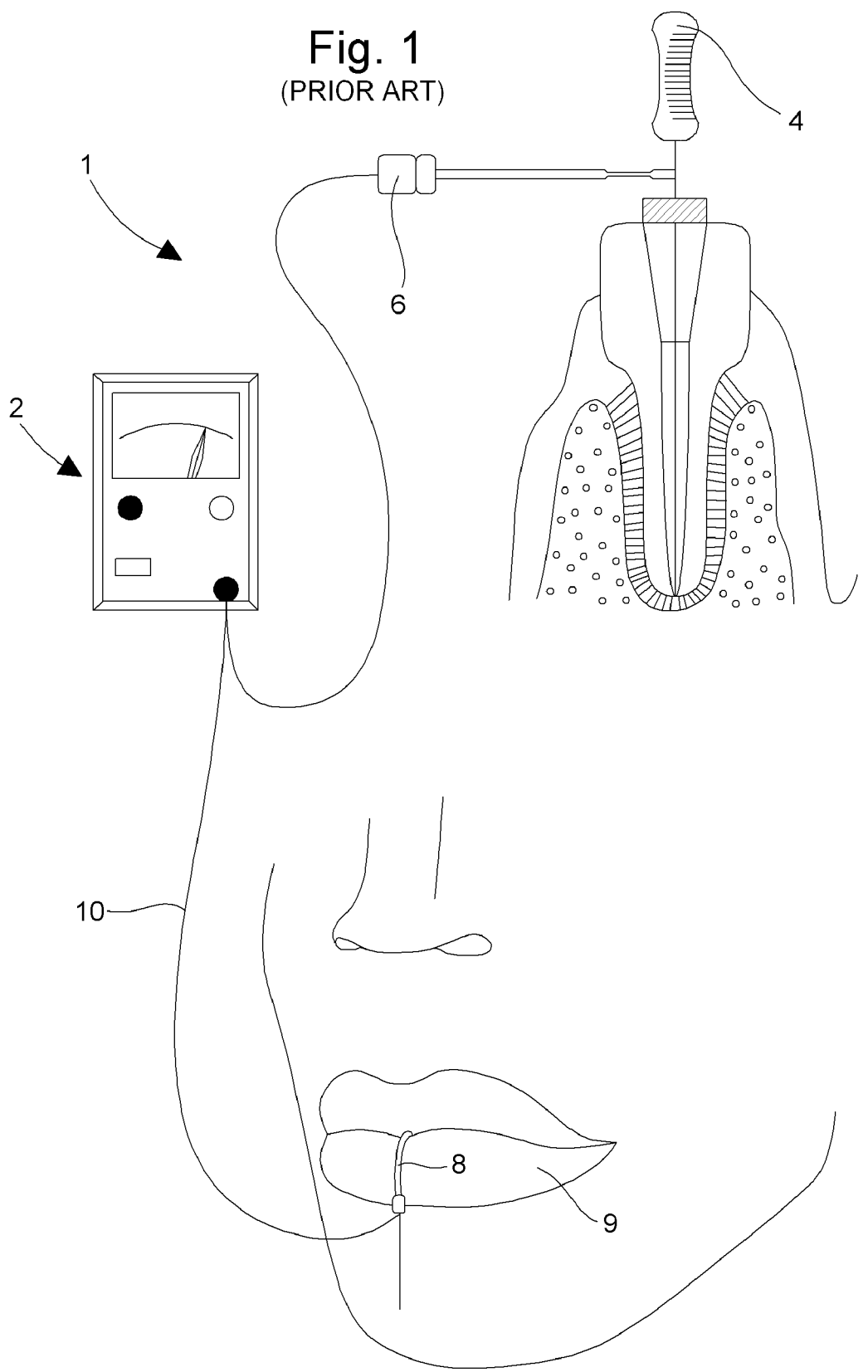
FIG. 1, already cited, is a schematic diagram of the wired connection of an apex locator apparatus according to the prior art.

The present invention proceeds from the general inventive idea consisting in providing an accessory for an apex locator apparatus, this accessory generally taking the form of a fitting held against the tooth to be treated or against a neighbouring tooth by appropriate means and which includes means for connection to the apex locator apparatus. In its widest sense, the connection between said apex locator apparatus and said fitting is a wireless connection, for example by radio frequency waves, which removes any problem of wired connection and provides the practitioner with total freedom of movement. In a simplified approach of the invention, the fitting includes wired connecting means between the apex locator apparatus and the endodontic tool on the one hand, and between said apparatus and the patient on the other hand. By thus grouping the connector technology linked to the use of an apex locator apparatus in a discrete element placed in the patient's mouth, the electrical connecting wires can be grouped together in a single bundle, which makes the practitioner's work easier, since he is less inconvenienced by the wires and has more freedom of movement. Moreover, the fitting according to the invention can be used with any type of apex locator apparatus operating in accordance with any of the three known detection modes based either on a resistance measurement, an impedance measurement, or a frequency measurement, and it does not require the purchase of any specific tools.

FIGS. 2A to 2C are views that illustrate a first embodiment of the present invention. FIG. 2A is a perspective view of the side of the posterior face 12 of a tooth to be treated 14. This tooth 14 is fitted with a fitting according to the invention designated as a whole by the general reference number 16. As can be see upon examining FIG. 2A and even better in FIG. 2B which is a perspective view of the side of the anterior face 18 of tooth 14, the fitting 16 is a parallelepiped part whose dimensions are compatible with those of tooth 14 and it is held against said tooth 14 by means of a tightening band 20. This tightening band 20 may be specially devised for holding fitting 16 according to the invention. However, according to a preferred embodiment of the invention, tightening band 20 is of the type that every practitioner has available and which is usually used for inserting dental amalgams. Tightening band 20 is passed around tooth 14, then fitting 16 is hooked onto said band 20 via hooking means 22 of the small tongue type that is slid between band 20 and tooth 14. Finally, band 20 is tightened again to hold fitting 16 firmly against tooth 14.

The small hooking tongue 22 extends parallel to and at a distance from the posterior face 24 of fitting 16, thereby delimiting a gap 26 into which a second contact strip 28 projects (see FIG. 2C). This contact strip 28 is a substantially Z-shaped spring part moulded into the mass of fitting 16 and including two contact lugs 30 and 32, the first 30 being in contact with tightening band 20, whereas the second 32 is in contact with an electrical connecting wire 34. A first end 34a of this wire 34 is moulded into the mass of fitting 16, whereas the second end 34b will be connected to the apex locator apparatus 2 shown in FIG. 1. As tightening band 20 is itself in contact with tooth 14, the electrical connection between the patient and the apex locator apparatus is thus achieved.

The fitting 16 includes a first contact strip 36. This is a contact flange including one generally U-shaped branch 38, which extends substantially parallel to the top face 40 of the tooth and which is extended vertically by a foot 42, whose free end is moulded in the mass of fitting 16. Foot 42 of contact flange 36 is in contact with an electrical connection wire 44 a first end 44a of which is moulded in the mass of fitting 16, whereas the second end 44b will be connected to the apex locator apparatus. During treatment, the practitioner will take care to apply his tool 46 against contact flange 36 so as to make the electrical connection between said tool 46 and the apex locator apparatus. Tool 46 may be a hand held tool or a contra angle. One could envisage the apex locator apparatus emitting a light or acoustic signal to indicate to the practitioner that tool 46 is actually in contact with flange 36. It will be noted that the two electrical connection wires 34 and 44 are joined in the same sheath 48 which facilitates the practitioner's movements particularly by preventing him becoming caught on a wire. Of course, according to a variant, one could envisage providing the ends 34a, 44a of connecting wires 34, 44 with male plugs that would be inserted in corresponding female plugs moulded into the mass of fitting 16. Likewise, flange 36 could be plugged into fitting 16. In such case, polarizing slot means would have to be provided in order to orientate said flange 36 in a suitable manner.

With reference to FIGS. 3A and 3B we will examine an alternative embodiment of the means for maintaining fitting 16 against said tooth 14. According to this variant, the maintaining means include a substantially U-shaped part 50 including a first portion 50a which abuts against the posterior face 12 of tooth 14 and which is connected via a connecting portion 50b to a second portion 50c which abuts against fitting 16 to keep the latter pressed against the anterior face 18 of tooth 14 by the effect of elastic deformation. The advantage of this embodiment is that it does not require any tools to secure fitting 16 against tooth 14. Those elements that are identical to those described with reference to FIGS. 2A and 2C are designated by the same reference numerals in FIGS. 3A to 3C and will not therefore be described again here. The presence of a metal fitting 53 should be noted, moulded in the mass of fitting 16 and in contact with the end 44a of the electrical connection wire on the one hand and with tooth 14 on the other hand, in order to provide the electrical connection between the patient and the apex locator device. It will also be noted that posterior face 24 of fitting 16 is curved so as to better match the tooth's profile.

With reference to FIGS. 4A to 4c we will now examine an alternative embodiment of the electrical connecting means between the endodontic tool 4 and the apex locator device. Those elements that are identical to those described with reference to FIGS. 2A to 2C will be designated by the same reference numerals and will not be described further hereafter. According to this embodiment, the electrical connection means include an induction coil 54. The turns 54a of coil 54 extend around tooth 14 in substantially parallel planes to the top face 40 of tooth 14. The two ends 54b and 54c of coil 54 are moulded in the mass of fitting 16 and are in electrical contact with two electrical connecting wires 53 and 55. Causing an electrical current to flow in turns 54a of coil 54 creates a variable magnetic field which induces a current in tool 4. The circuit is closed via tool 4, which, by coming into contact with tooth 14, allows the current to flow via electrical connecting wire 34. It is thus possible to induce a current in tool 4 without any contact, which considerably simplifies the practitioner's work.

Figure 5:
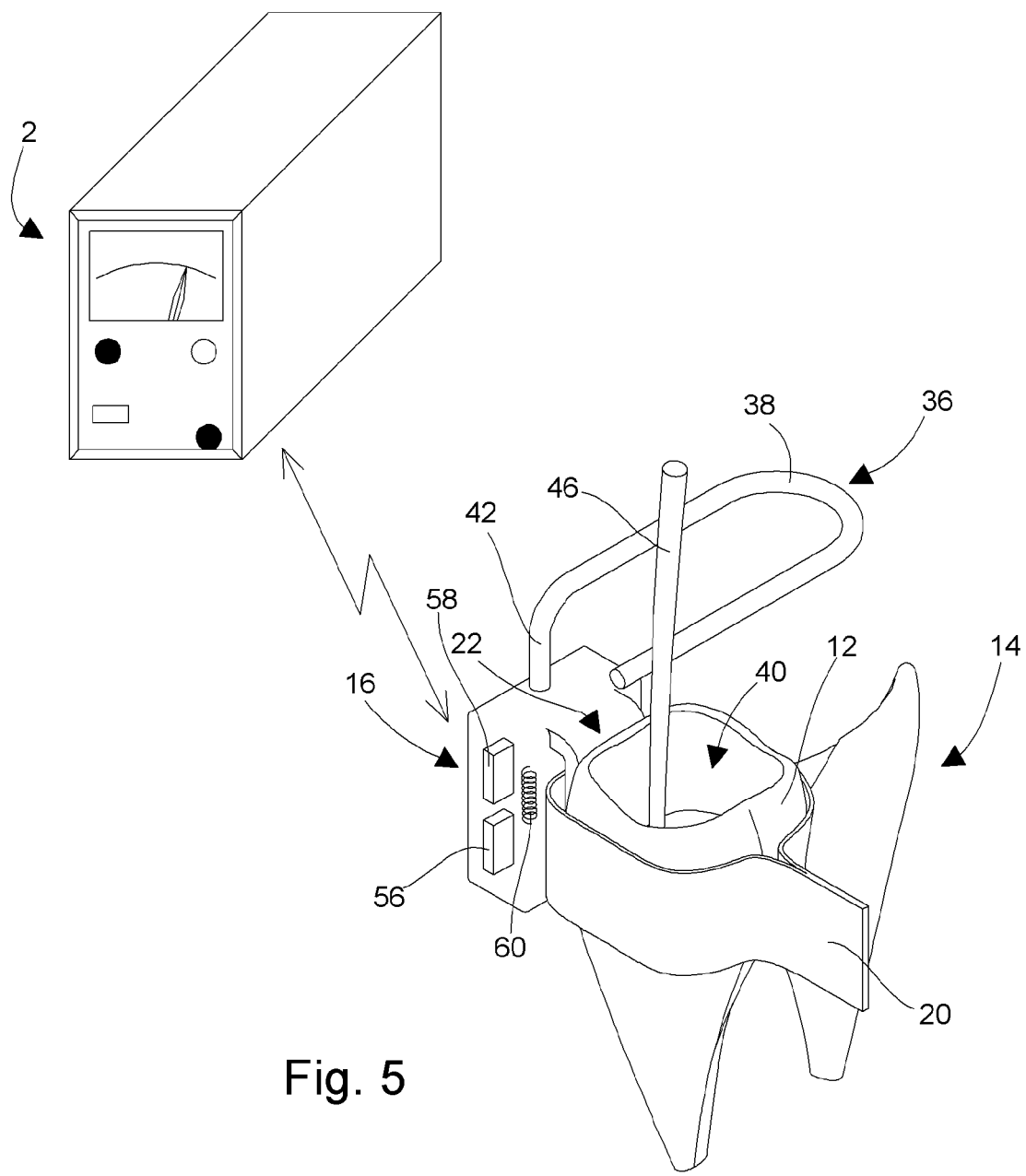
FIG. 5 is a perspective view showing the wireless connection between the apex locator apparatus and the fitting according to the invention.

It goes without saying that the present invention is not limited to the embodiments that have just been described, and that various simple alterations and variants can be envisaged by those skilled in the art without departing from the scope of the invention as defined by the annexed claims. In particular, one could envisage completely omitting any wired connection between fitting 16 and apex locator device 2 as illustrated in FIG. 5. In such case, the means for connecting apex locator device 2 and fitting 16 are wireless connecting means, for example using radio frequency waves. Fitting 16 will thus typically include at least one electronic measuring device including a circuit 56 for measuring a physical parameter representative of the relative position of endodontic tool 46 and the apex of tooth 14, this measuring circuit 56 being in particular associated with an analogue/digital converter for generating a digital measurement signal. The fitting will also include a transceiver circuit 58 for exchanging electromagnetic signals with the apex locator apparatus 2. The latter will have to be slightly modified to be able to emit signals in the direction of fitting 16 and to be able to pick up the signals emitted by said fitting 16 and to process them in order to be able to provide visual and/or acoustic data representative of the position of endodontic tool 46 relative to the apex of tooth 14. This will mean adapting apex locator 2 to an extent that is within the grasp of those skilled in the art and that will not therefore be described in more detail here. The processing of the signal emitted by fitting 16 may take place in apex locator 2. Measuring circuit 56 and transceiver circuit 58 may be of the passive type. In other words, they will be powered by a current induced in a coil 60 by the interrogation signal emitted by apex locator apparatus 2. Of course, fitting 16 could also include its own energy source. One could also envisage securing fitting 16 according to the invention on the posterior face of the tooth 14 to be treated or a neighbouring tooth. One could also fit contact strip 36 with an insulating sheath 62 over the entire length thereof except at the place where it is in contact with tool 46 in order to avoid the risk of short circuits between tooth 14 and the patient's cheek.

The invention claimed is:

1. An accessory for an apex locator apparatus, including a fitting comprising:
    (a) securing means for holding the fitting on a tooth to be treated or on a neighboring tooth;
    (b) first means, operably connected to an apex locator apparatus, for transmitting a signal between the apex locator apparatus and an endodontic tool; and
    (c) second means, operably connected to the apex locator apparatus, for transmitting a signal between the apex locator apparatus and a patient,
    wherein both the first and second means are located together in the fitting, and
    wherein the fitting is made of an electrically non-conductive material.

2. The accessory according to claim 1, wherein the first and second means for transmitting are wireless transmission means.

3. The accessory according to claim 2, wherein fitting further includes at least one circuit that measures a physical parameter indicative of a relative position of the endodontic tool and an apex of the tooth, and a transceiver circuit operably connected to the circuit that measures a physical parameter indicative to exchange signals with the apex locator apparatus.

4. The accessory according to claim 3, wherein the circuit that measures and the transceiver circuit are induction powered circuits.

5. The accessory according to claim 3, wherein the fitting includes a self-contained source of energy.

6. The accessory according to claim 1, wherein the first means is a wired electrical connection between the apex locator apparatus and the endodontic tool, and the second means is a wired electrical connection between the apex locator apparatus and a patient.

7. The accessory according to claim 1, wherein the securing means is a tightening band.

8. The accessory according to claim 1, wherein the securing means is an elastically deformable part.

9. The accessory according to claim 8, wherein the elastically deformable part includes a first portion disposed to abut against a posterior face of the tooth, a second portion disposed to hold the fitting pressed against an anterior face of the tooth, and a connecting portion connecting the first and second portion.

10. The accessory according to claim 9, wherein the elastically deformable part is a U-shaped part.

11. The accessory according to claim 6, wherein the second means comprises a contact strip disposed to establish an electrical connection between the apex locator apparatus and a patient, and the first means comprises another contact strip disposed to establish an electrical connection between the apex locator apparatus and the endodontic tool, and wherein the fitting further includes electrical connecting wires disposed to connect the contact strips with the apex locator apparatus and thus connect the apex locator apparatus to the fitting.

12. The accessory according to claim 11, wherein the securing means is a tightening band contacting the contact strip of the first means.

13. The accessory according to claim 12, wherein the fitting further includes a groove into which the tightening band passes, wherein the contact strip of the second means opens into the groove where it contacts the tightening band.

14. The accessory according to claim 11, wherein the securing means is an elastically deformable part and wherein the contact strip of the second means comes into contact with the tooth on which the fitting is secured via the elastically deformable part.

15. The accessory according to claim 14, wherein the fitting further includes a metal fitting disposed to ensure an electrical connection between the contact strip of the second means and the tooth on which the fitting is secured.

16. The accessory according to claim 11, wherein the contact strip of the first means is an electric contact flange that extends tangentially to the endodontic tool.

17. The accessory according to claim 16, wherein the contact strip of the first means is fitted with an insulating sheath over one part of a length thereof.

18. The accessory according to claim 11, wherein the first means further includes an induction coil that extends around the endodontic tool.

19. The accessory according to claim 18, wherein the contact strip of the first means and the induction coil are connected on the fitting or moulded in a mass of the fitting.

20. The accessory according to claim 1, wherein the fitting has a curved face to match a shape of an anterior face of the tooth against which the fitting is secured.

21. The accessory according to claim 1, wherein the fitting is made of a biologically compatible material.

22. The accessory according to claim 5, wherein the self-contained source of energy comprises an inductance coil disposed on the fitting.

23. The accessory according to claim 1, wherein wireless transceiver means is supported on the non-conductive fitting and comprises part of at least one of the first means and the second means.

24. A method of implementing an accessory for an apex locator apparatus, wherein the accessory includes a fitting including: (a) securing means for holding the fitting on a tooth to be treated or on a neighboring tooth; (b) first means, operably connected to an apex locator apparatus, for transmitting a signal between the apex locator apparatus and an endodontic tool; and (c) second means, operably connected to the apex locator apparatus, for transmitting a signal between the apex locator apparatus and a patient, wherein both the first and second means are located together in the fitting, wherein the method comprises the steps of:

(1) applying the endodontic tool against the fitting;
(2) producing an acoustic signal, an optical signal, or an acoustic signal and an optical signal from the apex locator apparatus when the endodontic tool is actually in contact with the fitting;
(3) indicating by the acoustic signal, an optical signal, or an acoustic signal and an optical signal to a practitioner that the endodontic tool is actually in contact with the fitting, and
(4) forming the fitting of an electrically non-conductive material.

* * * * *